US00PP27222P3

(12) United States Plant Patent
Hooper

(10) Patent No.: US PP27,222 P3
(45) Date of Patent: Oct. 4, 2016

(54) ***MAGNOLIA* PLANT NAMED 'CAMEO'**

(50) Latin Name: *Magnolia soulangeana*
Varietal Denomination: Cameo

(71) Applicant: Vance James Hooper, Waitara (NZ)

(72) Inventor: Vance James Hooper, Waitara (NZ)

( * ) Notice: Subject to any disclaimer, the term of this patent is extended or adjusted under 35 U.S.C. 154(b) by 359 days.

(21) Appl. No.: 13/999,335

(22) Filed: Feb. 13, 2014

(65) Prior Publication Data

US 2015/0230377 P1 Aug. 13, 2015

(51) Int. Cl.
*A01H 5/00* (2006.01)

(52) U.S. Cl.
USPC ..... Plt./223

(58) Field of Classification Search
USPC ..... Plt./223
CPC ..... A01H 5/02; A01H 5/00
See application file for complete search history.

(56) References Cited

PUBLICATIONS http://www.reimersnurseries.com/gallery/magnolia-2/magnolia-cameo-590by428/; Jun. 13, 2012; 1 page.*

* cited by examiner

*Primary Examiner* — Kent L Bell

(57) ABSTRACT

A new cultivar of *Magnolia* plant named 'Cameo' that is characterized by flowers having tepals with a red-purple under side and a white upper side, a long flowering season and flowering during the first year of growth.

2 Drawing Sheets

Botanical classification: *Magnolia soulangeana.*
Variety denomination: 'Cameo'

BACKGROUND OF THE INVENTION

The present invention relates to a new and distinct cultivar of *Magnolia* plant botanically known as *Magnolia soulangeana* and hereinafter referred to by the cultivar name 'Cameo'.

The new cultivar is the product of a breeding program conducted by the inventor in a cultivated area of Waitara, New Zealand. The objective of the breeding program is to develop new *Magnolia* cultivars that have unusual flower colors.

'Cameo' is a hybrid that originated from the female or seed parent *Magnolia soulangeana* 'Sweet Simplicity' (not patented) and the male or pollen parent *Magnolia soulangeana* 'Black Tulip' (not patented). The crossing was conducted in 1996 in a controlled environment. The cultivar 'Cameo' was selected by the inventor in 2000 as a single plant within the progeny of the stated cross in a cultivated area of Waitara, New Zealand.

Asexual reproduction of the new cultivar 'Cameo' by budding was first performed in 2000 in Waitara, New Zealand. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Magnolia* cultivar 'Cameo'. These traits in combination distinguish 'Cameo' as a new and distinct cultivar.

1. *Magnolia* 'Cameo' exhibits flowers having tepals with a red-purple under side and a white upper side.
2. *Magnolia* 'Cameo' exhibits a long flowering season.
3. *Magnolia* 'Cameo' exhibits flowers during the first year of growth.

The closest comparison varieties are *Magnolia* 'Iolanthe' (not patented) and 'Ruby' (not patented).

'Cameo' is different than 'Iolanthe' in having flowers with tepals with darker under sides, a more compact habit and earlier flowering. The flowers of 'Iolanthe' have flowers with tepals with light pink under sides.

'Cameo' is different than 'Ruby' in having more rounded flowers, flowers that retain color longer before fading, a more compact habit and earlier flowering. The flowers of 'Ruby' quickly fade to a silver-pink color.

In comparison to the parent plants, 'Cameo' is different than the female parent 'Sweet Simplicity' in having larger diameter branches and darker red-purple colored tepal under sides.

'Cameo' is different than the male parent 'Black Tulip' in having thinner diameter branches and tepal upper sides that are white. The flowers of 'Black Tulip' are purple-red on both sides.

BRIEF DESCRIPTION OF THE DRAWING

The accompanying photographs illustrate the distinguishing traits of *Magnolia* 'Cameo'.

Figure 1:
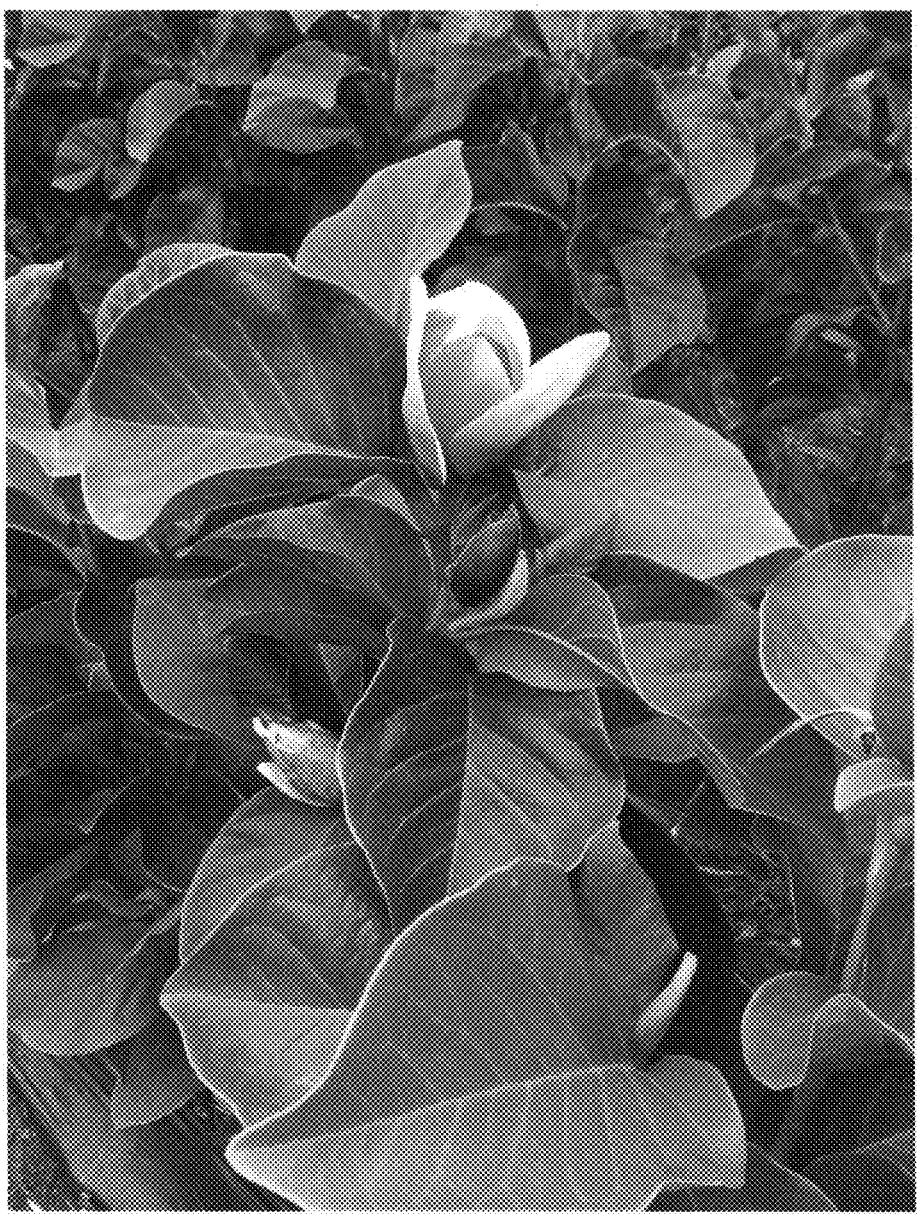
FIG. 1 shows an 18 month old plant with leaves and flower buds.
Figure 2:
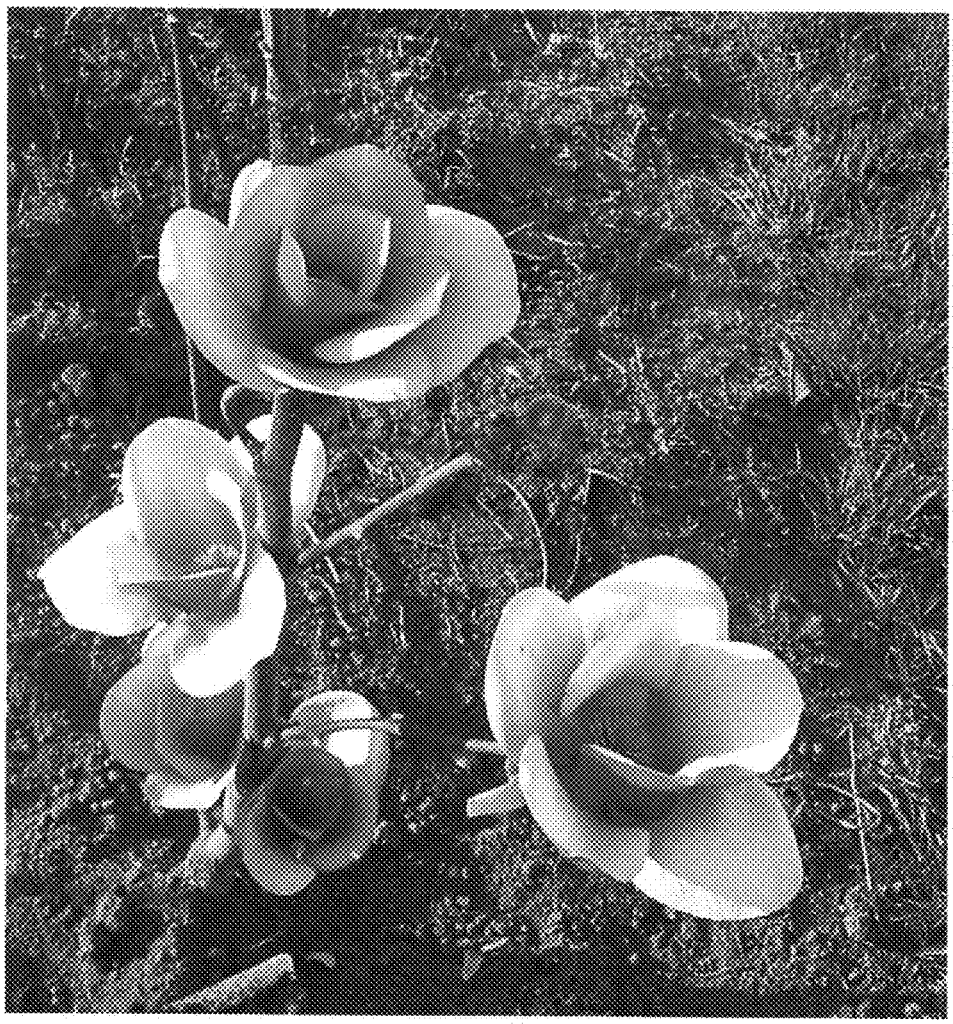
FIG. 2 shows a view of the plant with fully opened flowers.

The photographs were taken using conventional techniques and although colors may appear different from actual colors due to light reflectance it is as accurate as possible by conventional photographic techniques.

BOTANICAL DESCRIPTION OF THE PLANT

The following is a detailed description of the new *Magnolia* cultivar named 'Cameo'. Data was collected in Waitara, New Zealand from 18 month old field grown plants. The time of year was Autumn and the average temperature was 18 to 25° Centigrade during the day and 6 to 12° Centigrade at night. Color determinations are in accordance with The Royal Horticultural Society Colour Chart 2001 edition, except where general color terms of ordinary dictionary significance are used. The growing requirements are similar to the species. 'Cameo' has not been tested under all possible conditions and phenotypic differences may be observed with variations in environmental, climatic, and cultural conditions, however, without any variance in genotype.

Botanical classification: *Magnolia soulangeana* 'Cameo'.
Use: Ornamental Tree.
Parentage: 'Cameo' is a hybrid of the female or seed parent *Magnolia soulangeana* 'Sweet Simplicity' and the male or pollen parent *Magnolia soulangeana* 'Black Tulip'.
Vigor: Moderately strong.
Growth rate: 1 meter per year in young plants, 10 to 20 cm. per year in mature plants.
Growth habit: Upright.
Plant shape: Broad columnar.
Height: Average 1.0 m. in height.
Width: Average 35 cm. in width.
Hardiness: −15° to 40° C.
Propagation: Field budding.
Crop time: 2 years.
Stem:
- *Branching habit.*—Primary branching upward with shorter secondary branching.
- *Number of lateral branches.*—10 secondary branches.
- *Lateral branch diameter.*—4 to 5 mm. in diameter.
- *Lateral branch length.*—2.5 to 8 cm. in length.
- *Lateral branch strength.*—Moderately strong.
- *Stem color.*—Immature stems 145A, mature stems 200A.
- *Pubescence.*—Short hairs present on young branches.
- *Internode length.*—1.5 to 3 cm. between nodes.
- *Shape.*—Round.
- *Surface*—Smooth.
- *Lenticels.*—1 to 2 mm. in length, color 156C, density 1 per square cm.

Foliage:
- *Leaf arrangement.*—Alternate.
- *Compound or single.*—Single.
- *Quantity of leaves per lateral branch.*—5 to 10.
- *Leaf shape.*—Ovate.
- *Leaf apex.*—Acute.
- *Leaf base.*—Cuneate.
- *Leaf length.*—13 to 15 cm. in length.
- *Leaf width.*—9 to 10 cm. in width.
- *Pubescence.*—Present on undersides of leaves only.
- *Texture.*—Both surfaces slightly leathery.
- *Leaf margin.*—Entire.
- *Vein pattern.*—Reticulate.
- *Young leaf color* (*upper surface*).—146C.
- *Young leaf color* (*lower surface*).—146C.
- *Mature leaf color* (*upper surface*).—137A.
- *Mature leaf color* (*lower surface*).—137C.
- *Vein color* (*lower surface*).—145A.
- *Vein color* (*upper surface*).—137A.
- *Leaf attachment.*—Petiolate.
- *Petiole dimensions.*—1.7 cm. in length, 4 mm. in width.
- *Petiole color.*—144A.
- *Durability of foliage to stress.*—High.

Flower:
- *Flower arrangement.*—Cup shaped flowers held upright.
- *Quantity of flowers per lateral stem.*—1.
- *Quantity of flower buds per lateral stem.*—1.
- *Quantity of flowers and buds per plant.*—Approximately 7.
- *Flowering season.*—Spring to Summer.
- *Time to flower or response time.*—5 to 7 weeks after breaking dormancy.
- *Fragrance.*—Sweet citrus scent.
- *Self-cleaning or persistent.*—Self cleaning.
- *Flower bud length.*—28 mm. in length.
- *Flower bud diameter.*—15 mm. in diameter.
- *Flower bud shape.*—Ovate.
- *Rate of bud opening.*—14 days.
- *Bud color.*—79C.
- *Flower aspect.*—Upright.
- *Flower shape.*—Cup shaped.
- *Flower dimensions.*—13 cm. in diameter and 9 cm. in height.
- *Flower longevity.*—Lasts approximately 4 to 6 days on plant.
- *Tepal arrangement.*—Whorled.
- *Number of tepals.*—9 to 12 in number.
- *Fused or unfused.*—Not fused.
- *Tepal shape.*—Obovate.
- *Tepal margin.*—Entire.
- *Tepal apex.*—Acute.
- *Tepal base.*—Rounded.
- *Tepal texture.*—Outer surface smooth, inner surface veined.
- *Tepal dimensions.*—11 cm. in length and 9 cm. in width.
- *Tepal color when opening* (*upper side*).—N155A frosted with 72B.
- *Tepal color when opening* (*under side*).—Varies from 79C at base to 71A at tip.
- *Tepal color when fully opened* (*upper side*).—N155A frosted with 72B.
- *Tepal color when fully opened* (*under side*).—Varies from 79C at base to 71A at tip.
- *Tepal color fading to.*—Under side fading to 71D.

Peduncle:
- *Peduncle dimensions.*—4 mm. in length and 10 mm. in diameter.
- *Peduncle angle.*—Vertical.
- *Peduncle color.*—146C.

Reproduction organs:
- *Stamen number.*—60 to 80.
- *Anther shape.*—Curved.
- *Anther length.*—18 mm. in length.
- *Anther color.*—Center 79C, base and tip 83A.
- *Amount of pollen.*—Moderate.
- *Pollen color.*—2D.
- *Pistil number.*—1 in number.
- *Stigma shape.*—Curved.
- *Stigma color.*—55B at base, 56C at tip.

*Ovary*.—Ovaries grouped into a column 18 to 25 mm. in length.

*Ovary color*.—192B.

Fruit:

*Shape*.—Cone.

*Quantity*.—4 to 6 cones.

*Dimensions*.—10 cm. in length and 3 cm. in diameter.

*Texture*.—Smooth with raised lenticels.

*Color*.—138B, turning 46C when ripe.

Seed:

*Quantity*.—1 or 2 seeds per ovary.

*Seed dimensions*.—11 mm. in length and 9 mm. in diameter.

*Seed color*.—202A.

Disease and pest resistance: Plants of the new *Magnolia* have not been observed for disease or pest resistance.

The invention claimed is:

1. A new and distinct variety of *Magnolia* plant named 'Cameo' as described and illustrated.

* * * * *